(12) United States Patent
Tanaka et al.

(10) Patent No.: US 7,343,038 B2
(45) Date of Patent: Mar. 11, 2008

(54) METHOD FOR EVALUATING CONTAMINATION ON SURFACE OF OBJECT AND IMAGING BOX USED FOR THE METHOD

(75) Inventors: Hirokazu Tanaka, Osaka (JP); Daisuke Arai, Osaka (JP); Toshiaki Anzaki, Osaka (JP); Takashi Ikuno, Osaka (JP); Kazuhiro Doushita, Osaka (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 856 days.

(21) Appl. No.: 10/484,943

(22) PCT Filed: Jul. 25, 2002

(86) PCT No.: PCT/JP02/07526

§ 371 (c)(1),
(2), (4) Date: Jan. 26, 2004

(87) PCT Pub. No.: WO03/010525

PCT Pub. Date: Feb. 6, 2003

(65) Prior Publication Data

US 2004/0175026 A1 Sep. 9, 2004

(30) Foreign Application Priority Data

Jul. 27, 2001 (JP) .............................. 2001-227224
Jul. 30, 2001 (JP) .............................. 2001-262374

(51) Int. Cl.
*G06K 9/00* (2006.01)
*G06K 9/40* (2006.01)

(52) U.S. Cl. ........................ 382/168; 382/141; 382/275
(58) Field of Classification Search ........ 382/141–152, 382/162, 168, 232, 260, 275; 398/71, 544
See application file for complete search history.

(56) References Cited

U.S. PATENT DOCUMENTS

| 4,574,393 A | * | 3/1986 | Blackwell et al. .......... 382/162 |
| 6,052,534 A | | 4/2000 | Goto |
| 6,487,321 B1 | * | 11/2002 | Edgar et al. ................ 382/260 |
| 2002/0125319 A1 | * | 9/2002 | Sasaki et al. ............... 235/454 |

FOREIGN PATENT DOCUMENTS

JP 49-89428 A 8/1974

(Continued)

OTHER PUBLICATIONS

International Search Report, Nov. 19, 2002.

Primary Examiner—Duy M. Dang
(74) Attorney, Agent, or Firm—RatnerPrestia

(57) ABSTRACT

There is provided a method for evaluating the contamination by quantifying the surface contamination of an object such as a window glass plate, a wall, or the like in such a manner that the quantified value is close to the visual sensation of human being. The method comprises the steps of taking a color image of the surface of the object, converting a color image data denoting the color image into a monochromatic image data, dividing a monochromatic image denoted by the monochromatic image data into a dot matrix to obtain lightness per dot, selecting an area to be evaluated on the dot matrix, calculating a standard deviation of lightness from the distribution of lightness of the selected area.

13 Claims, 20 Drawing Sheets

FOREIGN PATENT DOCUMENTS

| | | |
|---|---|---|
| JP | 2-128147 A | 5/1990 |
| JP | 5-81697 U1 | 11/1993 |
| JP | 63-142239 A | 6/1998 |
| JP | 11-64970 A | 3/1999 |
| JP | 2001-41899 A | 2/2001 |
| JP | 2002-168792 A | 6/2002 |

* cited by examiner

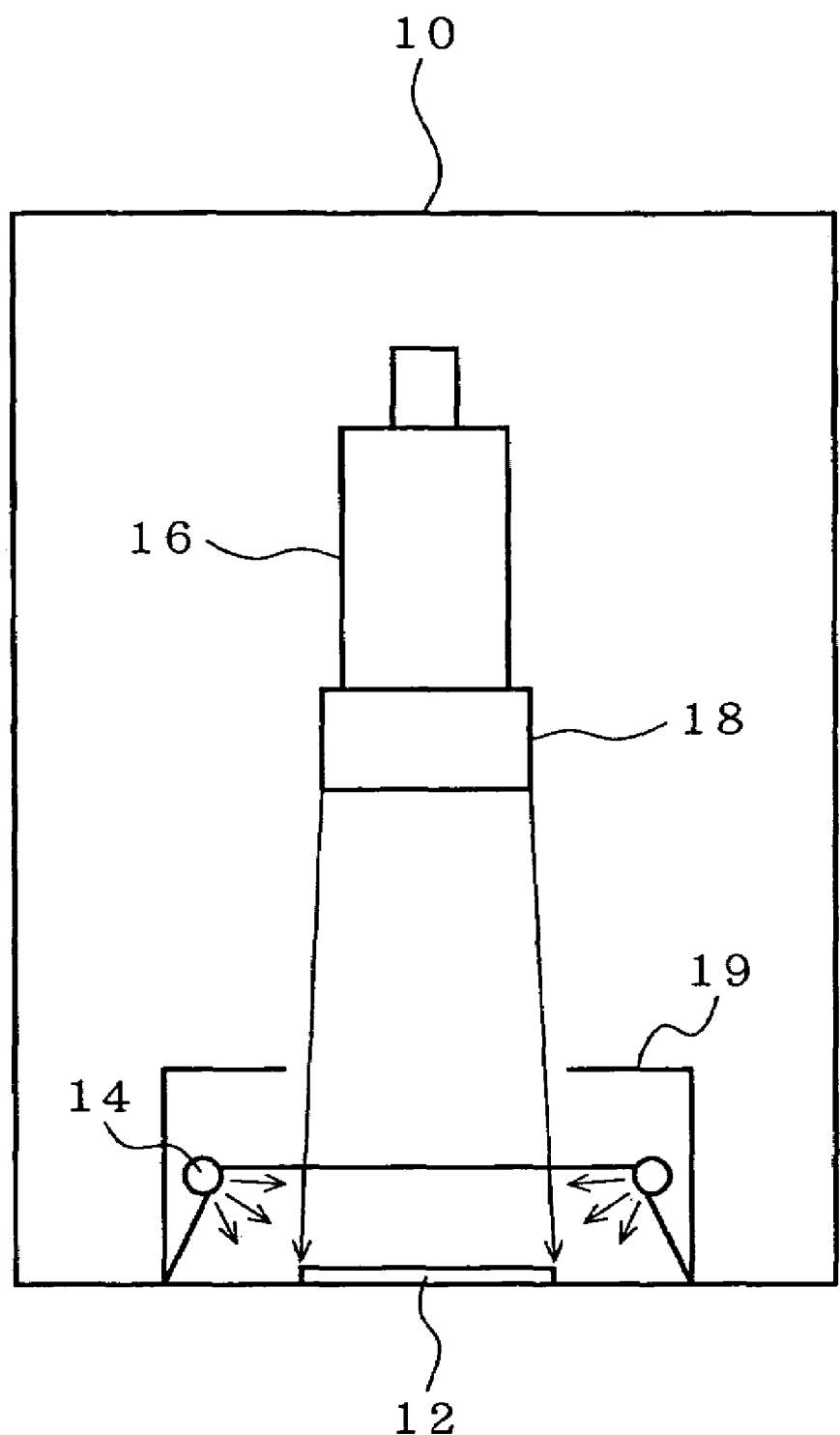
F I G. 1

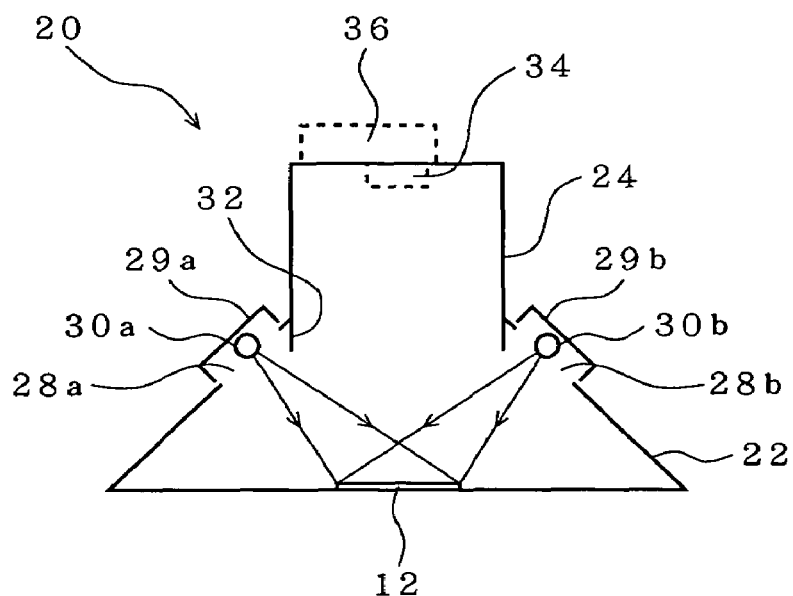
F I G. 2 A
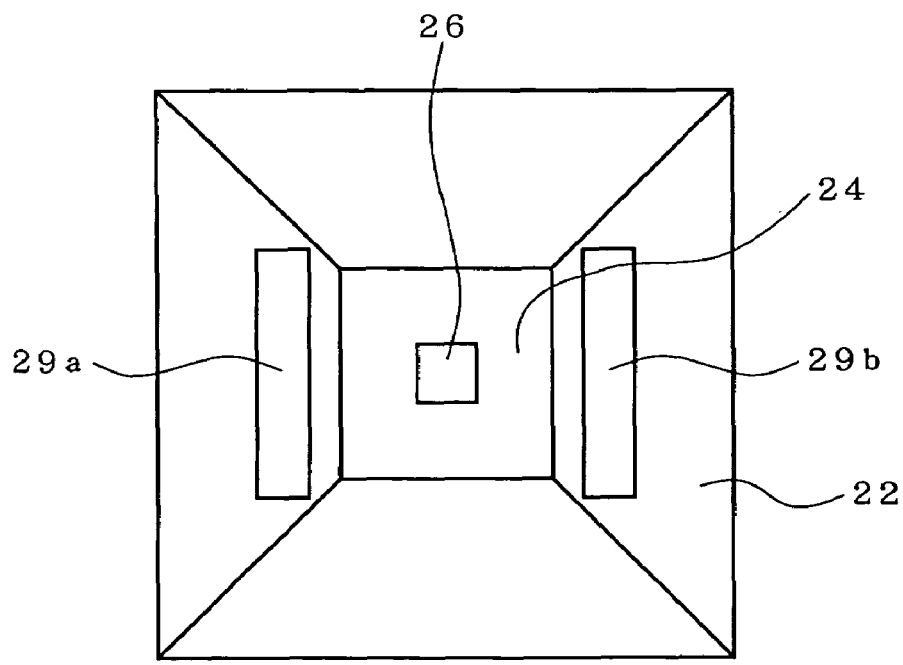
F I G. 2 B

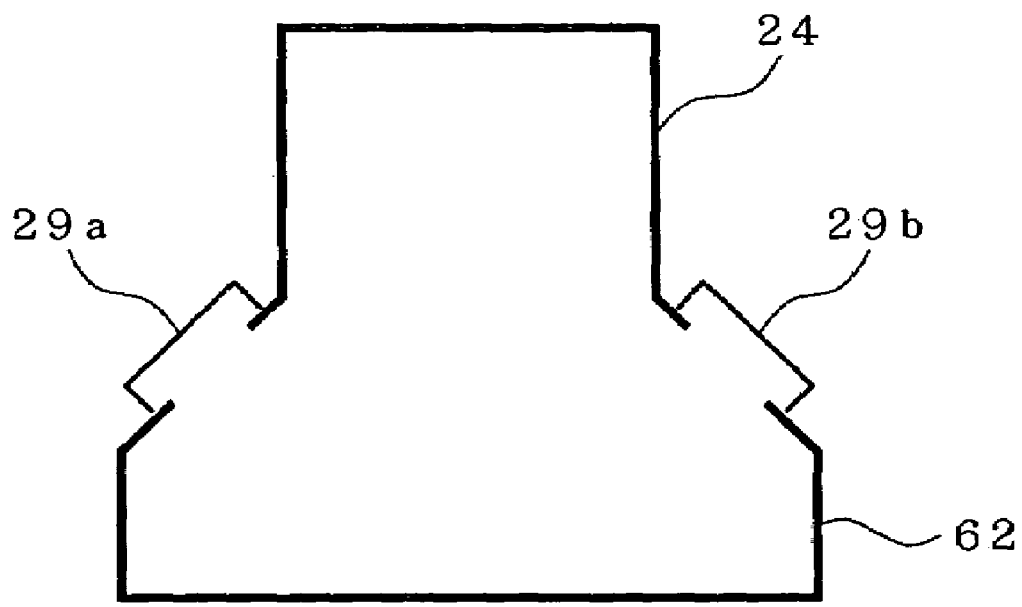
F I G. 1 0 A
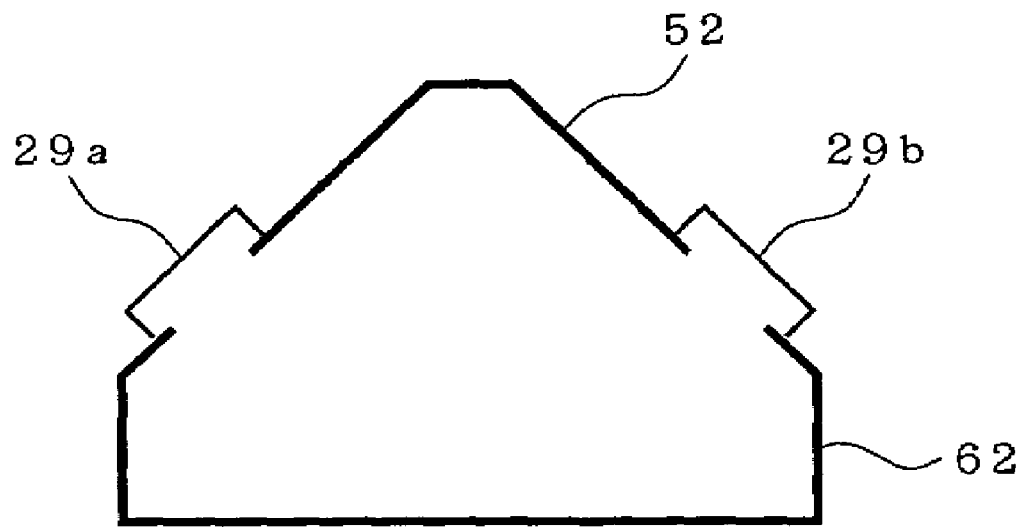
F I G. 1 0 B

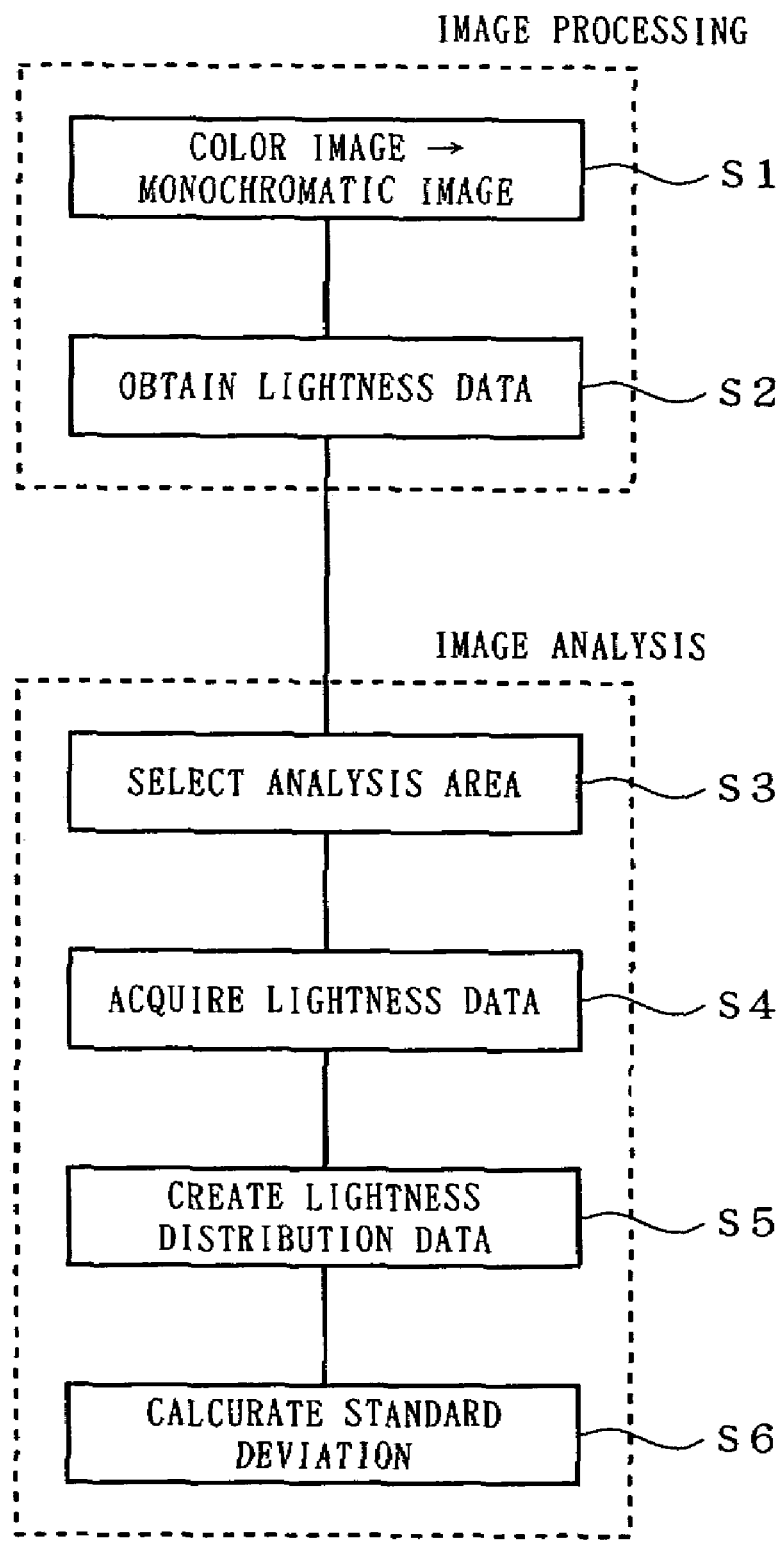
F I G. 13

SELF-CLEANING GLASS PLATE
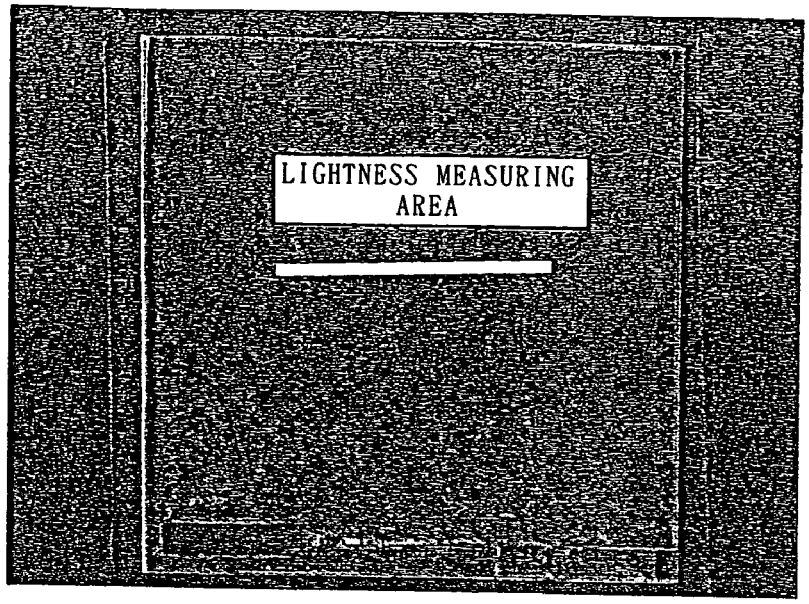
F I G . 1 6 A
FLOAT GLASS PLATE
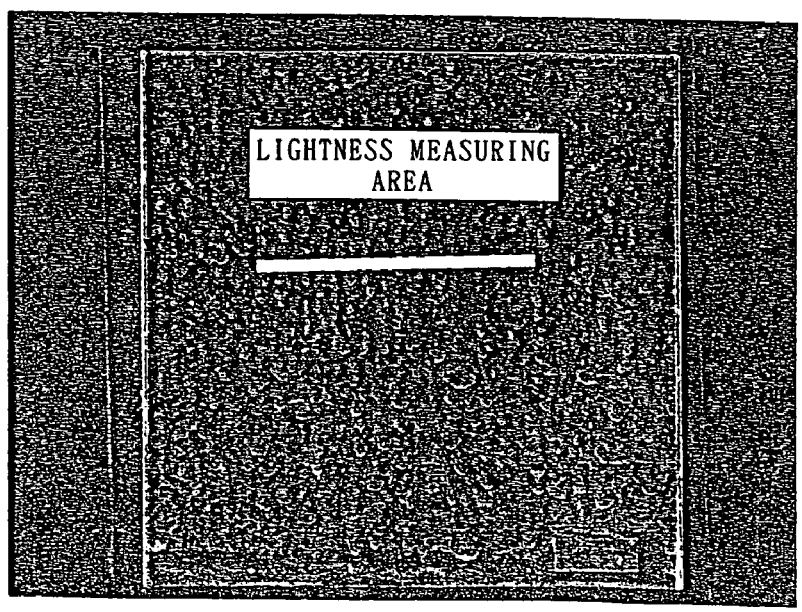
F I G . 1 6 B ORDINARY GLASS PLATE
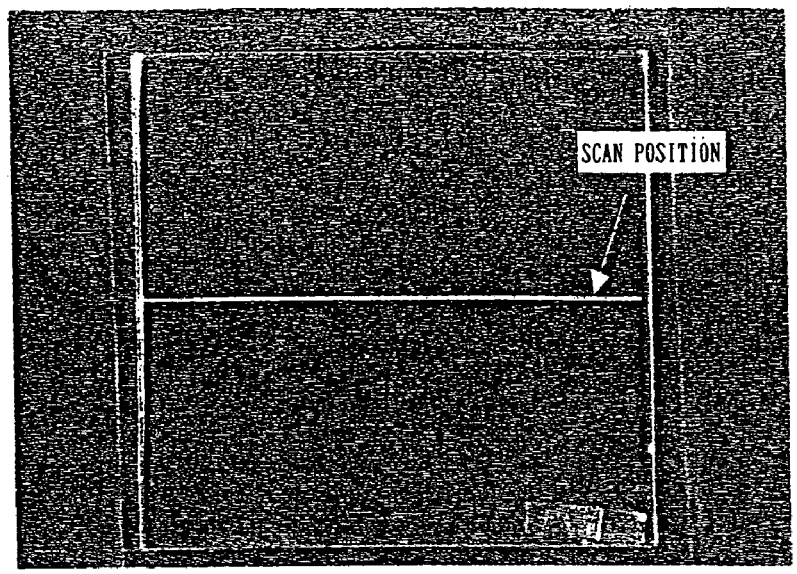
F I G . 1 9 A
GLASS PLATE HAVING SCRATCHES
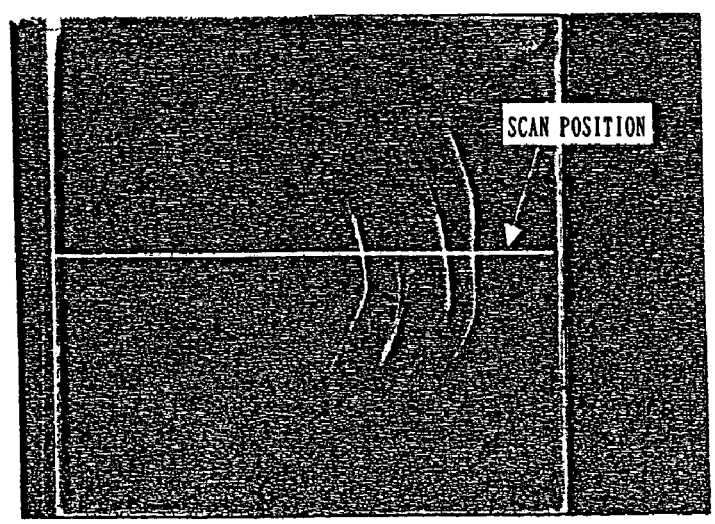
F I G . 1 9 B

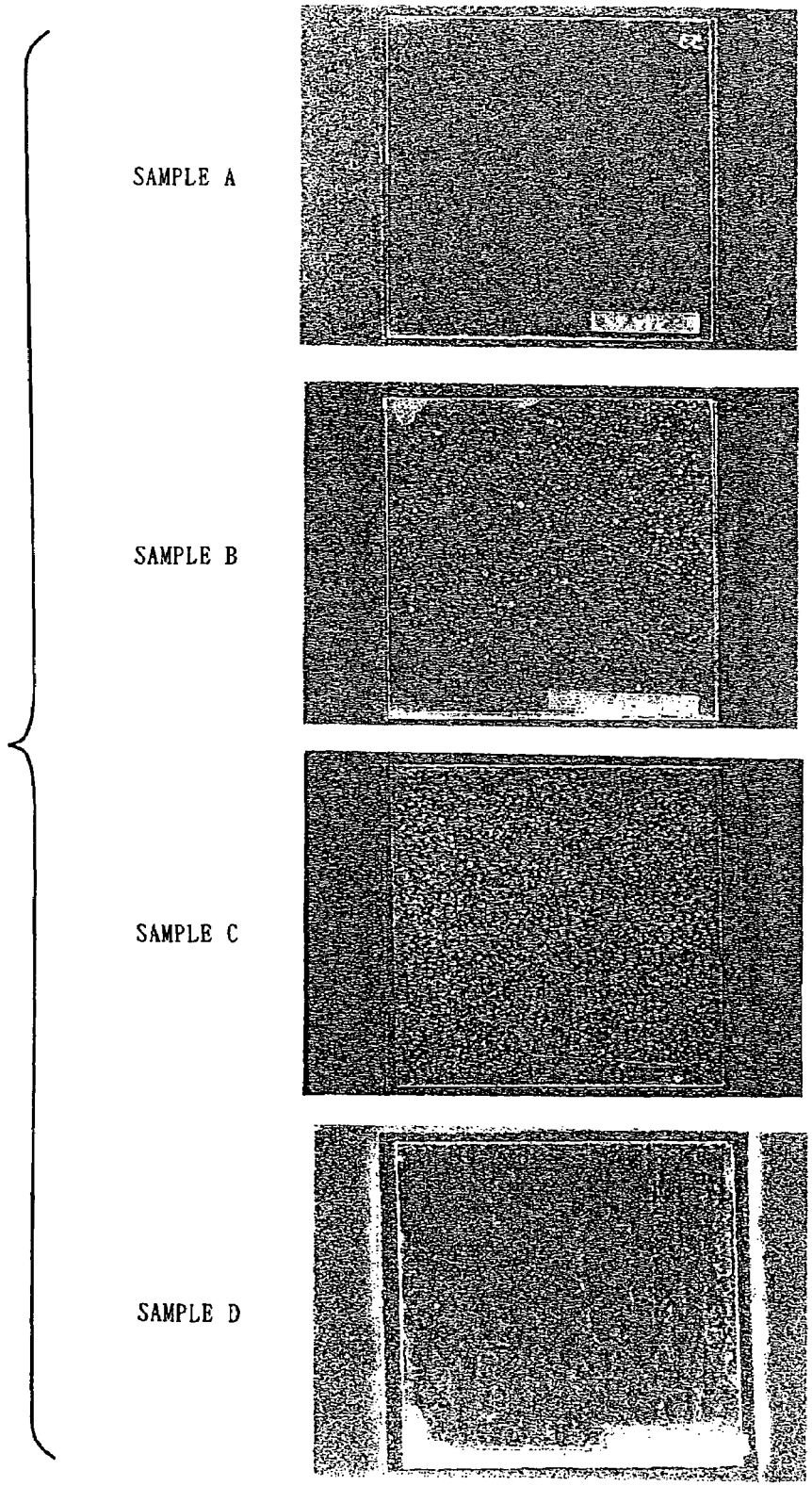
F I G. 2 1

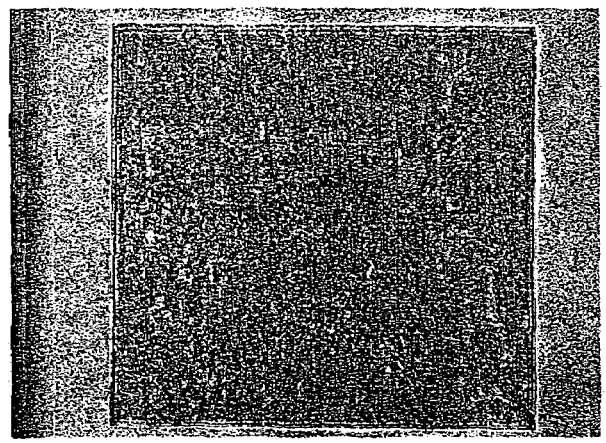
SAMPLE E
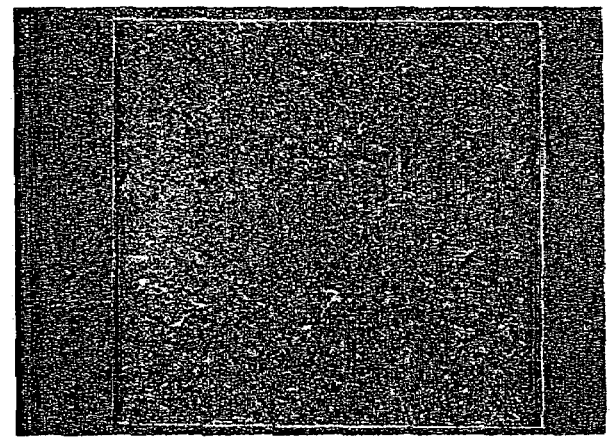
SAMPLE F
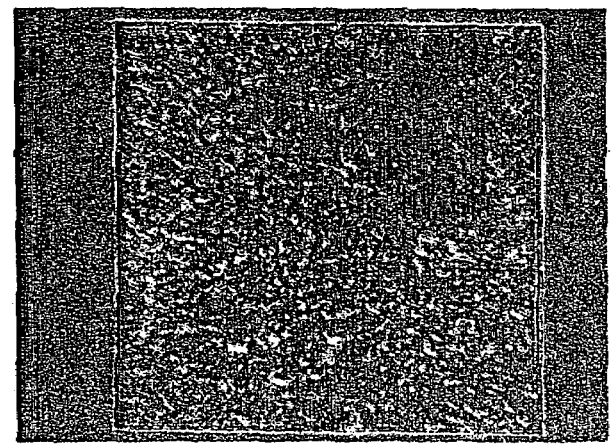
SAMPLE G
F I G . 2 2

CONTAMINATION INDEX 50.8
SECOND CONTAMINATION INDEX 47.1

CONTAMINATION INDEX 53.2
SECOND CONTAMINATION INDEX 50.2

CONTAMINATION INDEX 48.4
SECOND CONTAMINATION INDEX 53.0

METHOD FOR EVALUATING CONTAMINATION ON SURFACE OF OBJECT AND IMAGING BOX USED FOR THE METHOD

TECHNICAL FIELD

The present invention relates to a method for evaluating the contamination due to contaminants, surface scratches, color unevenness, and the like on a surface of an object such as a plate, a wall, or the like composed of glass, plastic, etc, particularly to a method for evaluating the contamination based on the distribution of lightness on a surface of an object. The present invention further relates to an imaging box used in the contamination evaluation method, particularly to an imaging box used for taking a clear image of a surface of a plate or wall without taking images of a background and a camera itself reflected on the surface of a plate or wall.

BACKGROUND ART

A surface of a window glass plate, a wall, or the like is usually contaminated by dusts or surface scratches thereon. A conventional method for evaluating the contamination is a visual inspection by an inspector. However, the evaluation by a visual inspection may not be quantified and has a miserable repeatability, because the evaluation results are dispersed among inspectors and may not be recorded.

As an evaluation method which replaces a visual evaluation, quantitative methods have been proposed such as a method for measuring optical characteristics (color difference, glossiness, luminance, haze factor, transmittance, etc) of an object to be evaluated, and a method for measuring the mass (weight) of deposits on a surface of an object.

The conventional quantitative methods as described above measure average data (i.e., surface average data for a measured area) of the optical characteristics of an object or the mass of deposits on an object. The average data do not include factors such as fine distribution and the like, so that it does not match to the visual sensation of human being for the aggregation of contamination and unevenness due to deposits and fine surface scratches.

For measuring the optical characteristics of an object to be evaluated, an image of a surface of an object is taken by means of an ordinary optical camera. In the case of taking an image of a contaminated surface of a glass plate made of a transparent material of a high reflectivity mounted in a building, it is difficult to take a clear image of the contaminated surface of the glass plate, because the images of a background and a camera itself reflected on the glass plate are taken by the camera. When an image of the surface of the glass plate is taken from a direction oblique thereto by a camera in order to prevent the reflected image of the camera itself from being taken, correct image information for the contaminated surface is not obtained.

In order to resolve these-problems, the following settings are required, i.e., (1) an object only is uniformly and brightly illuminated by a light source, and the light reflected on the object does not impinge upon a camera, and (2) a camera is positioned in front of an object, but the reflected light is prevented from impinging upon a camera in order not to take an image of the camera itself reflected on the surface of the glass plate.

Referring to FIG. 1, there is shown a conventional system for taking an image in a dark room in which an object, a ring light source and a camera are arranged. In a dark room 10, there are arranged an object 12, a ring fluorescent lamp 14 for illuminating the object 12, and a cover 19 for the fluorescent lamp to prevent the light from the lamp from directly impinging upon a lens 18 of a CCD camera 16.

According to this conventional system, it is possible to obtain a clear image of a surface of the object, because all of the components are arranged in the dark room so that taking the images of a background and the camera itself reflected on the surface of the object 12 is prevented, and the light reflected on the object 12 does not impinge upon the lens 18.

When an image of the contamination due to contaminants, scratches, color unevenness, and the like on a glass plate is intended to be taken using the conventional system, it requires much time to set dedicated jigs and devices.

The conventional system also has no portability and mobility, and may not take an image of an upright glass plate and a glass plate mounted in a building.

DISCLOSURE OF INVENTION

An object of the present invention is to provide a method for evaluating the contamination by quantifying the surface contamination of an object such as a window glass plate, a wall, or the like in such a manner that the quantified value is close to the visual sensation of human being.

Another object of the present invention is to provide an imaging box having portability and mobility used for such a contamination evaluation method, the imaging box allowing the setting of the condition for taking an image of the surface contamination (contaminants, scratches, color unevenness) of a plate member, a wall member, or the like without taking the reflected images of a camera itself and a background.

A first aspect of the present invention is directed to a method for evaluating the contamination of a surface of an object. The method according to the present invention is carried out in following steps. It should be noted hereinafter that the contamination by deposition of dusts is referred to as "deposition contamination", and the contamination by fine scratches is referred to as "scratch contamination", if necessary to distinguish therebetween.

1. An image data is obtained by taking an image of a surface of an object to be evaluated.

An image of a surface of an object is taken by an imaging device to obtain an image data which is transferred to an image processing apparatus such as a personal computer. As an imaging device, a solid state imaging device such as a CCD (Charge Coupled Device) camera, a CMOS (Complementary Metal Oxide Semiconductor) camera, or an ordinary optical camera may be used. When a solid state imaging device is used, the image data may be directly transferred to an image processing apparatus. When an optical camera is used, a photograph may be read by an image scanner to obtain an image data which is transferred to an image processing apparatus.

2. A processing of an image data and an analysis of lightness distribution are conducted in an image processing apparatus.

1) An area where the contamination looks like severe by a visual inspection in an image displayed on a display of an image processing apparatus is preferentially selected. That is, an area to be evaluated is optionally selected by an inspector.

2) The size of minimum unit in an analysis of lightness distribution of an image is varied dependent on the size of deposition contamination or scratches contamination. That is, the size of minimum unit in an analysis of lightness distribution is selected so that the surface contamination is most effectively and efficiently represented.

3) A represented lightness data is analyzed and quantified to "contamination index" which is close to the visual sensation of human being.

A second aspect of the present invention is directed to an imaging box. According to the present invention, the most suitable positional relation among a camera, an object and a light source, and the most suitable illuminance condition are realized by one imaging box. The imaging box has a structure such that when an object is illuminated from an oblique direction to be uniform illuminance, the direct and reflected light is not reached to a camera.

A first embodiment of the imaging box according to the present invention comprises a first box-shaped envelope having an opening in which a lens portion of a camera is attached with being directed inward, an inner surface of the first envelope having a low reflectivity structure, a second box-shaped envelope in which an object is positioned in front of the lens portion, the second envelope including light source inside or outside thereof illuminating the object from oblique direction and an inner surface of the second envelope having a low reflectivity structure, and a light-shielding member, provided in the first envelope and/or the second envelope, for preventing direct and reflected light from the light source from impinging upon the lens portion of the camera, an inner surface of the light-shielding member having a low reflectivity structure, wherein the first and second envelopes construct together one space.

A second embodiment of the imaging box according to the present invention comprises a first box-shaped envelope having an opening in which a lens portion of the camera is attached with being directed inward, an inner surface of the first envelope having a low reflectivity structure, a second box-shaped envelope having a window opposed to the object in front of the lens portion, the second envelope including light source inside or outside thereof illuminating the object from oblique direction and an inner surface of the second envelope having a low reflectivity structure, a light-shielding member, provided in the first envelope and the second envelope, for preventing direct and reflected light from the light source from impinging upon the lens portion of the camera, an inner surface of the light-shielding member having a low reflectivity structure, wherein the first and second envelopes construct together one space.

BRIEF DESCRIPTION OF DRAWINGS

FIG. 1 shows a conventional system for taking an image in a dark room in which an object, a ring light source and a camera are arranged.

FIGS. 2A and 2B show a cross-sectional view and plan view illustrating a fundamental structure of an imaging box according to the present invention.

FIGS. 10A and 10B show another structures of an object illuminating envelope, respectively.

FIG. 13 shows a flow chart illustrating an image processing and analysis by mean of the personal computer 30.

FIGS. 16A and 16B show the monochromatic images of the self-cleaning glass plate and ordinary float glass plate displayed on a display, respectively.

FIGS. 19A and 19B show the monochromatic images of an ordinary glass plate having no scratches and an ordinary glass plate having scratches.

FIG. 21 shows the photographs of samples A, B, C and D.

FIG. 22 shows the photographs of samples E, F, and G.

BEST MODE FOR CARRYING OUT THE INVENTION

Figure 3:
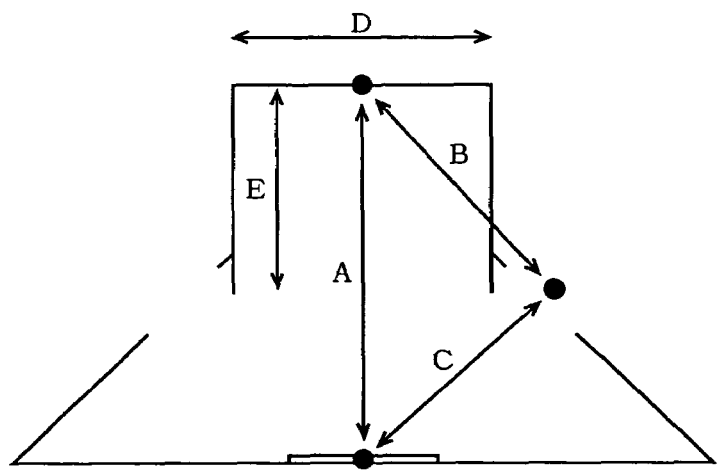
FIG. 3 shows a positional relation among components in FIG. 2.

An embodiment of a method for evaluating the contamination according to the present invention will now be described for a glass plate as an example of object to be evaluated. An image of a surface of a glass plate is taken by a CCD camera. In order to obtain a clear image of the surface of a glass plate, a dedicated imaging box is provided in front of a lens portion of the camera. The imaging box comprises a light source and light-shielding plates for preventing light from impinging upon a lens portion of the camera, the light including light direct from the light source and light reflected on the surface of a glass plate.

FIGS. 2A and 2B show a cross-sectional view and plan view illustrating a fundamental structure of an imaging box according to the present invention. An imaging box 20 consists of an object illuminating envelope 22 and an image conducting envelope 24, both of them being box-shaped. The shape of the object illuminating envelope 22 is truncated pyramid, and that of the image conducting envelope 24 is cube or rectangular parallelepiped. A black cloth of low reflectivity and non-gloss is stuck to all the inner surface of the envelopes 22 and 24.

An opening 26 for a camera lens portion is opened in the center of a top wall of the image conducting envelope 24, and openings 28a and 28b are opened in two opposed side walls of the object illuminating envelope 22. A camera 36 is mounted on the top wall of the envelope 24 in such a manner that a lens portion 34 thereof is fitted into the opening 26 to be faced to an object 12. The object 12 is positioned in front of the lens portion 34, i.e., at the center of a bottom wall of the object illuminating envelope 22.

Light source devices 29a and 29b are mounted on the openings 28a and 28b such that the devices cover the openings. The light source devices comprise line fluorescent lamps 30a and 30b, respectively. In this embodiment, these fluorescent lamps are positioned outside the object illuminating envelope 22. The light from each fluorescent lamp illuminates uniformly the object 12 at an angle of 45° from both opposed sides.

A light-shielding plate 32 is provided as an extended portion of the lower side wall of the image conducting envelope 24, which is extending into the object illuminating envelope 22. A black cloth of low reflectivity and non-gloss is stuck on all the surface of the light-shielding plate.

Referring to FIG. 3, there is shown a positional relation among components of the imaging box. The distance A between the camera lens potion 34 and the object 12 is 300 mm. Each of the fluorescent lamps 30a and 30b is positioned at the vertex of a rectangular equilateral triangle with the distance A being a bottom side and distances B, C being residual two sides. The length D of one side of a square viewed from the point above the image conducting envelope 24 is selected to be ⅔ times the distance A, i.e., 200 mm. The height E of the side wall including the light-shielding plate 32 is set to be ½ times the distance A, i.e., 150 mm.

As an example, a glass plate sample of 100 mm×100 mm is prepared as an object 12, a digital camera having a lens the diameter thereof is 50 mm and a zoom ratio thereof is 1-3 is used, and an inverter-type line fluorescent lamp of 27 W (the length thereof is 100 mm) is used as a light source to select the brightness thereof so that the illuminance of the object 12 is more than 10000 lux.

In the imaging box described above, the glass plate sample 12 is imaged by the CCD camera in a suitable exposure value with a zoom ratio being regulated so that the view of the sample is fully expanded in a finder of the camera.

As the amount of incident light to the camera lens portion 34 by the direct light and reflected light from the light source is extremely less and thus the camera lens portion is not reflected in the glass plate sample, not only the camera lens portion itself but also the direct light and reflected light from the light source are not imaged by the CCD camera. Therefore, a clear image of the surface of the glass plate sample may be obtained.

The above-described imaging box 20 is used for taking an image of an object positioned in the imaging box. Next, an embodiment of an imaging box which is used for taking an image of a window glass plate mounted in a building will be described.

Figure 4:
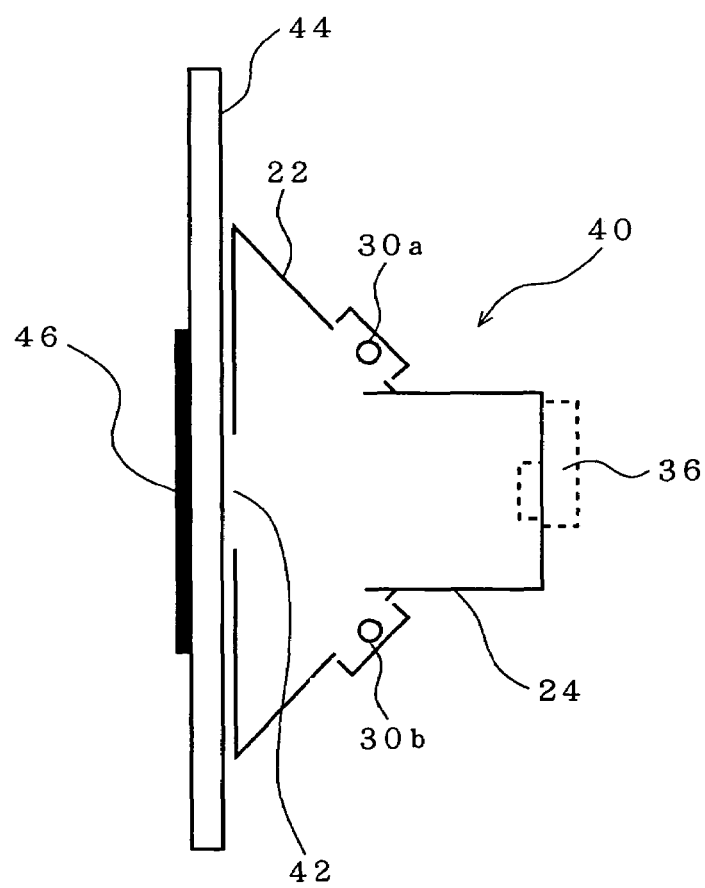
FIG. 4 shows a cross-sectional view of an imaging box used for taking an image of a window glass plate mounted in a building.

Such an imaging box 40 is shown in FIG. 4 in a cross-sectional view. The imaging box is different from that shown in FIGS. 2A and 2B in that a window 42 is opened in the bottom wall of an object illuminating envelope. The components that are common to that in FIGS. 2A and 2B are identified by the same reference numerals.

FIG. 4 also illustrates the case where an image of an outer surface of an upright window glass plate mounted in a building is taken by a CCD camera using the imaging box. The imaging box 40 having a CCD camera 36 attached thereto is positioned with the bottom wall of the envelope 22 being contacted to the outer surface of a window glass plate 44. A panel is positioned on the inner surface of the part of the window glass plate 44 to be imaged, a black cloth of low reflectivity and non-gloss being stuck to the panel. An image of the surface of the window glass plate is taken through the window 42 by the camera.

In the imaging boxes illustrated with reference to FIGS. 2 and 4, the light-shielding plate 32 is provided as an extended portion of the lower side wall of the image conducting envelope 24. However, there may be the cases where only the light-shielding plate 32 is not enough to shield the light. The structures of preferable light-shielding members will be described for various cases.

Figure 5:
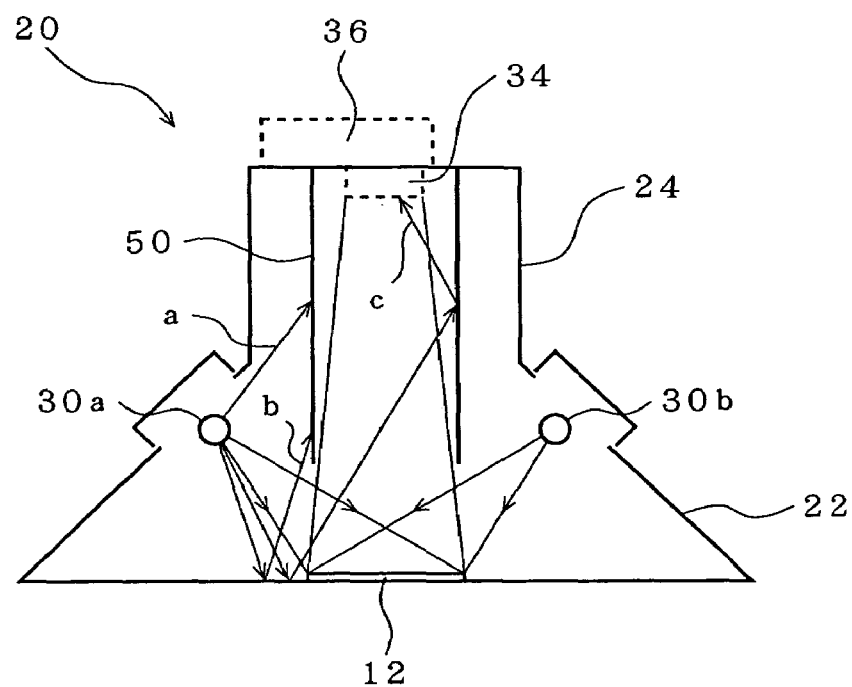
FIG. 5 shows an example of a light-shielding member.

Referring to FIG. 5, there is shown the case where the fluorescent lamps 30a and 30b are provided in the object illuminating envelope 22. A light-shielding member 50 for this case has a structure such that the direct light from the lamps and the primary light reflected on a surface the bottom wall of the envelope 22 are effectively shielded. The light-shielding member 50 consists of a cylinder having a circular or polygonal cross-section extending downward from the peripheral part of the lens portion 34. The position of the lower end of the light-shielding member is determined by the conditions such that (1) a field viewed from the lens portion 34 to the object 12 is not shield, (2) the light from the lamps 30a and 30b is not prevented from illuminating the object 12, and (3) the direct light from. the lamps 30a and 30b and the primary reflected light from the surface of the bottom wall of the envelope 22 are prevented.

In the light-shielding member 50 thus structured, the direct light a from the light source and the primary reflected light b are shielded, but the primary reflected light is further reflected on the inner surface of the light-shielding member 50 to become a secondary reflected light c which impinges upon the lens portion 34. It is assumed that the reflectivity of the cloth stuck on the inner surface of the imaging box is 2%, the light intensity of the secondary reflected light is at most 0.04% of the direct light. As the influence of the secondary reflected light is less, the light-shielding member 50 has an effect enough to prevent the lens portion itself from being imaged by the camera and prevent a fog due to the secondary reflected light.

Figure 6:
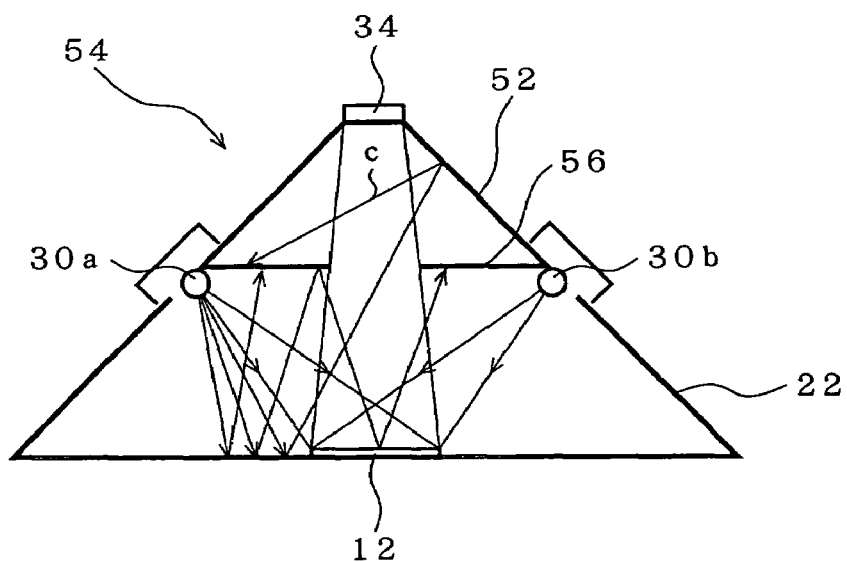
FIG. 6 shows an example of a light-shielding member.

Referring to FIG. 6, there is shown the structure of a light-shielding member suited to an imaging box 54 in which the side walls of the image conducting envelope 52 are inclined different from that in FIG. 2. The light-shielding member consists of a horizontal light-shielding plate 56 having a circular opening in a field viewed from the lens portion to the object. The word "horizontal" is used in the case that the imaging box of FIG. 6 is positioned vertically. Correctly speaking, the light-shielding plate is positioned perpendicularly to an optical axis of the lens of the CCD camera 36.

According to the horizontal light-shielding plate 56, even if the primary reflected light from the surface of the bottom wall of the object illuminating portion 22 is reflected on the inner surface of the image conducting envelope 52 to become a secondary reflected light c, the secondary reflected light is not reached to the lens portion 34 as the inner surface of the envelope 52 is inclined. In this imaging box, there is a risk such that a tertiary reflected light from the light-shielding plate impinges upon the lens. Assuming that the reflectivity of the cloth stuck on the inner surface of the imaging box is 2%, the light intensity of the tertiary reflected light is at most 0.0008% of the direct light, which may be neglected.

Figure 7:
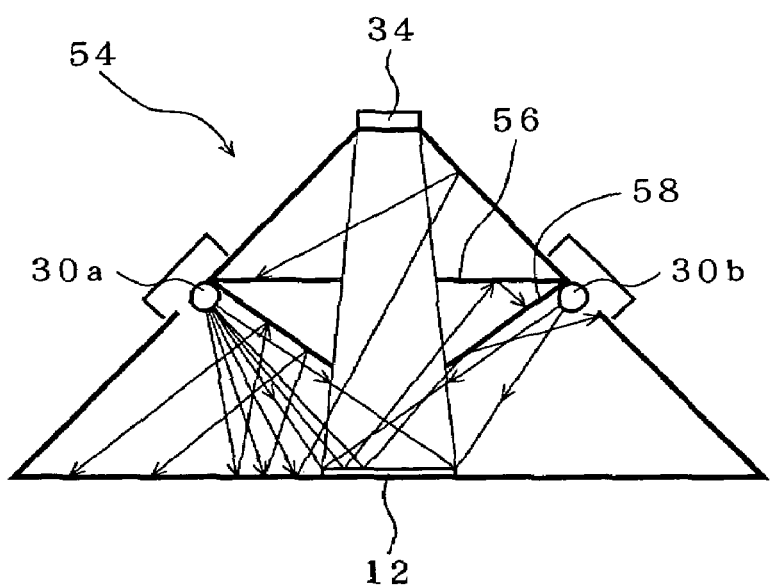
FIG. 7 shows an example of a light-shielding member.
Figure 8:
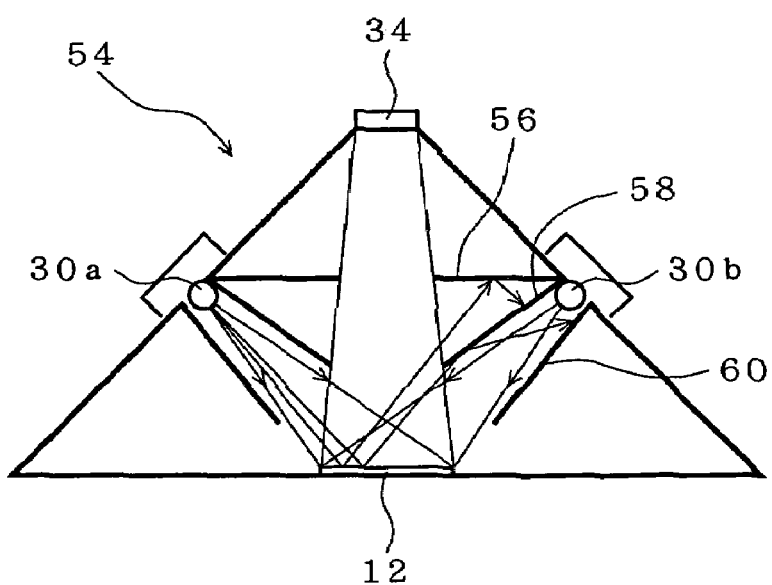
FIG. 8 shows an example of a light-shielding member.

FIG. 7 shows an example of an imaging box in which inclined light-shielding plates 58 are provided in addition to the horizontal light-shielding plate 56 in FIG. 6. FIG. 8 shows an example of an imaging box in which inclined light-shielding plates 60 are further provided in addition to the horizontal light-shielding plate 56 and the inclined light-shielding plates 58 in FIG. 7. According to this structure, the reflected light is not nearly reached to the lens portion due to the interaction of these light-shielding plates. This is because that the light which impinges between these light-shielding plates is reflected therebetween to be attenuated so that the intensity thereof is decreased substantially to zero.

Figure 9:
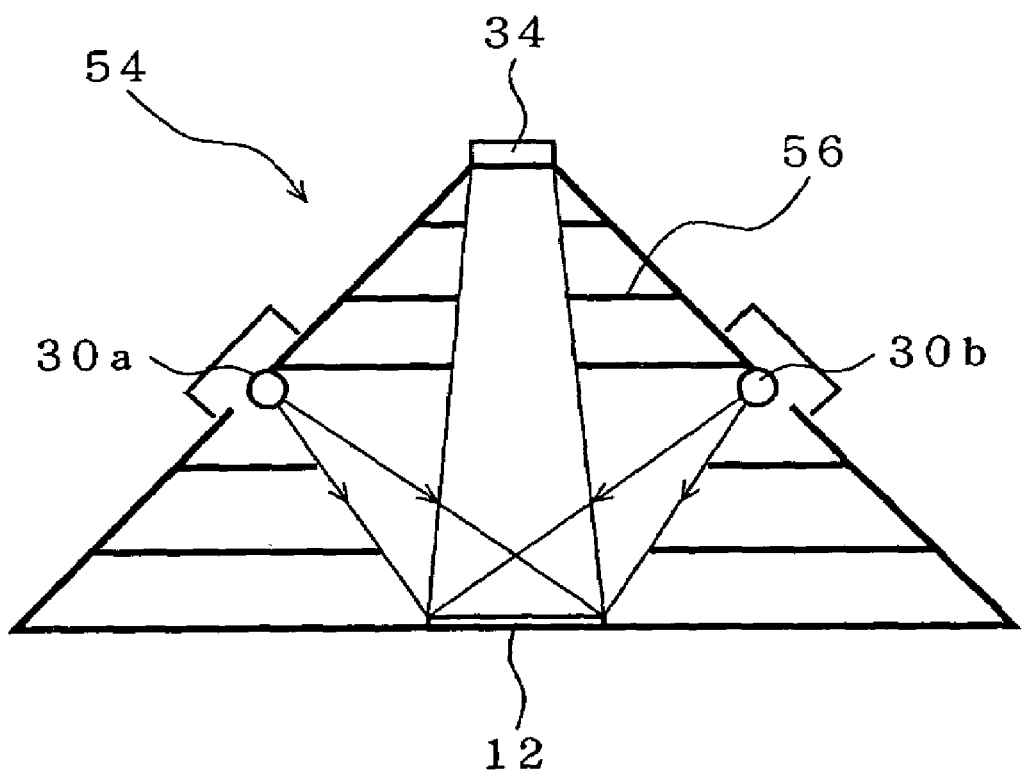
FIG. 9 shows an example of a light-shielding member.

An example of the structure in which the above-described effects may simply be realized is shown in FIG. 9. In this structure, a plurality of horizontal light-shielding plates 56 are provided. The horizontal light-shielding plates 56 are stucked as shown in the figure, so that the reflected light is attenuated and does not reach to the lens portion 34. It is also possible that inclined light-shielding plates may be combined to the plurality of horizontal light-shielding plates.

In each embodiment of the imaging boxes described above, the shape of the object illuminating envelope is truncated pyramid, and therefore the peripheral wall of the lower portion of the object illuminating envelope extends outward. If there is no such extended part, then the object illuminating envelope may be further compact. FIGS. 10A and 10B show the cross-sectional views of imaging boxes having the structure described above. The structure in FIG. 10A corresponds to the imaging boxes in FIGS. 2, 4 and 5, and the structure in FIG. 10B the imaging boxes in FIGS. 6, 7, 8 and 9. In FIGS. 10A and 10B, only the walls and light source devices are shown without the light-shielding member. Reference numeral 62 in the figures designates the object illuminating envelope.

Figure 11:
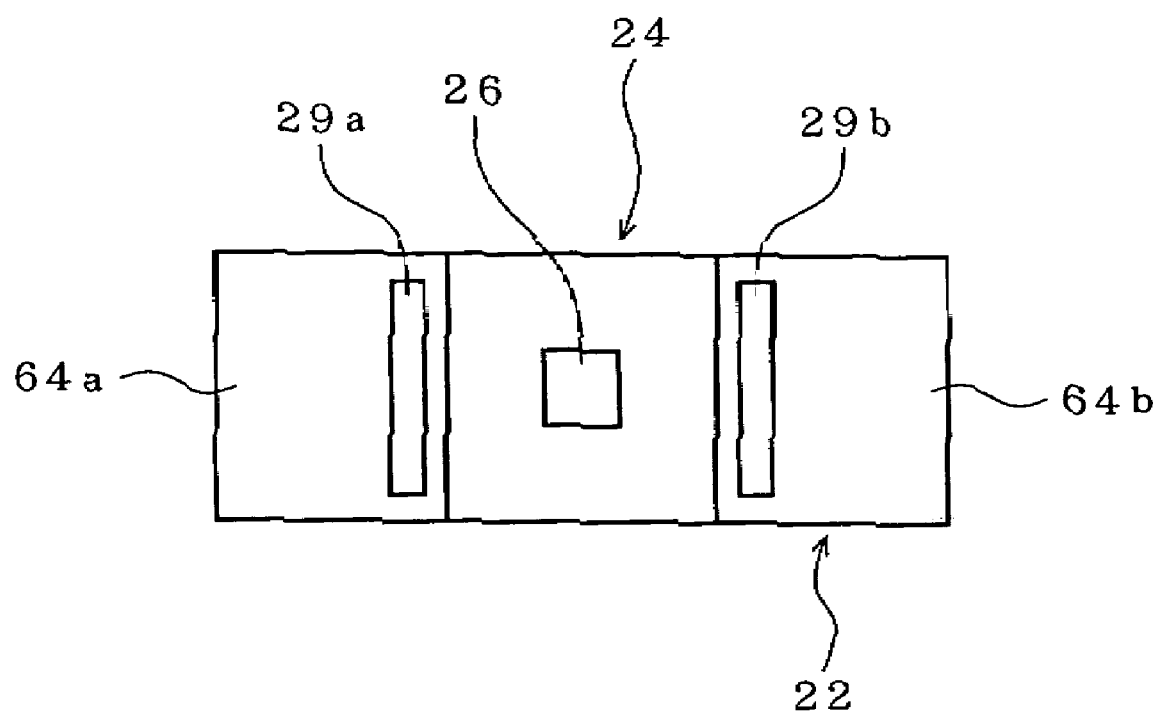
FIG. 11 shows still another structure of an object illuminating envelope.

Referring to FIG. 11, there is shown a plan view of a modification of the imaging box in FIG.2. In this modification, the walls to which the light source devices 29a and 29b are attached are inclined with respect to the optical axis of the lens, and residual walls are parallel with the optical axis of the lens. Reference numerals 64a and 64b denote the inclined walls on both sides of the object illuminating envelope.

While the imaging area of the object is 100 mm×100 mm in the imaging box of each embodiment described above, the imaging area may be extended by enlarging the size of the imaging box and increasing the amount of illumination of the light source. The positional relation among components in the imaging box may be realized by similarly enlarging a rectangular equilateral triangle with the distance A between the lens portion and the object being as a reference. The tolerance of ±10% may be allowed to the deviation of the shape of the triangle. Even if the positional relation among components is over the range of the tolerance, the requirement is satisfied where the direct light and the primary reflected light do not impinge upon the camera lens portion. While two line fluorescent lamps are used, one ring lamp may be used.

Each embodiment of the imaging box according to the present invention has been illustrated. Next, an embodiment of a method for evaluating the surface contamination of a window glass plate using such an imaging box will now be described in detail as an example.

It is assumed that the imaging box 40 in FIG. 4 is used. The CCD camera 36 is attached to the imaging box 40. The imaging box thus comprising the CCD camera is positioned with the window 42 thereof being contacted to one surface of the window glass plate 44 to be evaluated. A panel 46 covered by a black cloth of low reflectivity and non-gloss is contacted to the other surface of the window glass plate 44. A color image of the surface area of 100 mm×100 mm of the window glass plate is taken by the CCD camera.

Figure 12:
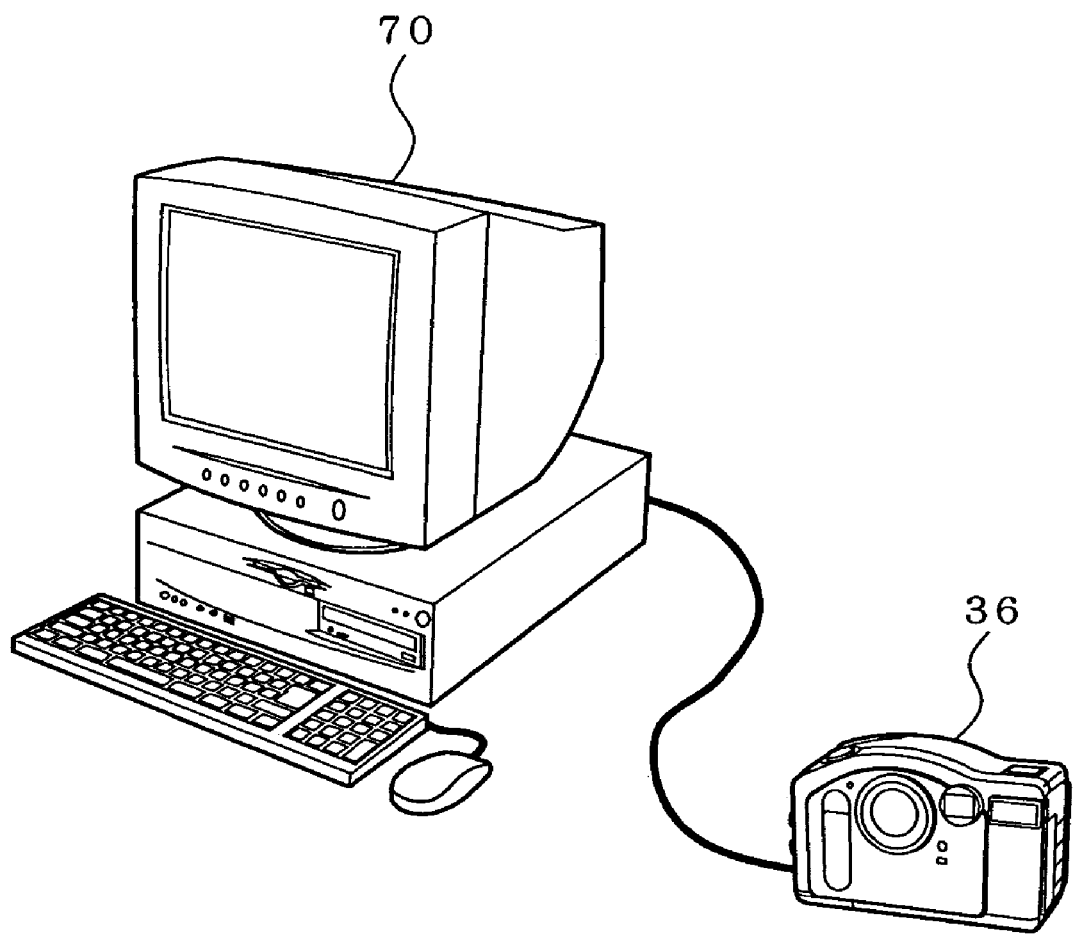
FIG. 12 shows a personal computer.

As shown in FIG. 12, the data for the color image taken by the CCD camera 36 is transferred to a personal computer 70 in a data format (JPG format, TIF format, etc.) supported by an image processing software. The personal computer 70 comprises a central processing unit and a memory.

An image processing and analysis is carried out by the personal computer 70 to obtain "contamination index". FIG. 13 shows a flow chart illustrating an image processing and analysis by means of the personal computer.

The color image data from the CCD camera 36 is stored in the memory of the computer 70. The color image denoted by the color image data may be displayed on a display to be observed by an inspector. The central processing unit reads the color image data from the memory to convert it into a monochromatic image data showing the lightness of the surface of the window glass plate (Step S1). The monochromatic image data is stored in the memory. A monochromatic image denoted by the monochromatic image data may be displayed on a display to be observed by an inspector.

Figure 14:
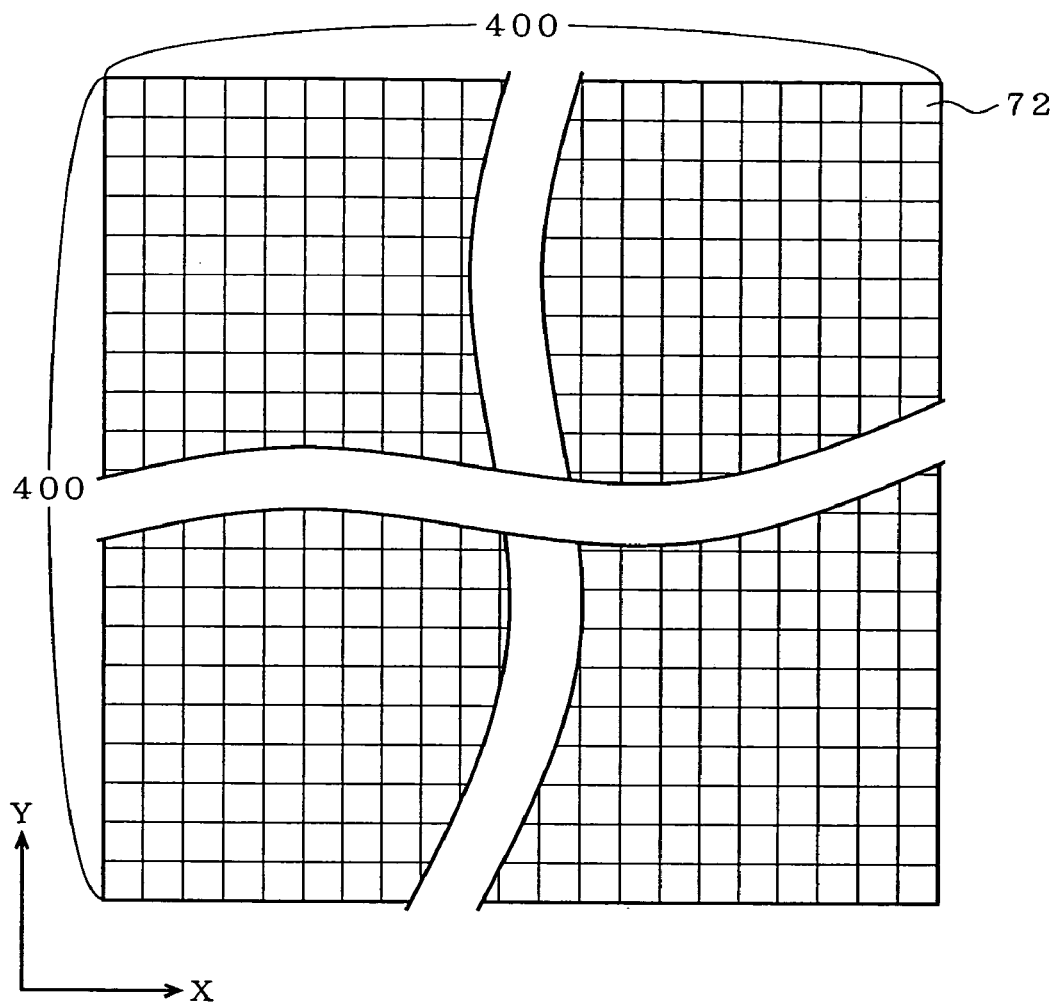
FIG. 14 shows a dot matrix.

The central processing unit reads the monochromatic image data from the memory to divide the monochromatic image of 100 mm×100 mm denoted by the monochromatic image data into 400×400 meshes as shown in FIG. 14, thereby forming a dot matrix in which a divided one region (0.25 mm×0.25 mm) is dealt as one dot. In FIG. 14, an X-Y coordinate is shown to indicate the extending directions of the dot matrix. One dot 72 is a minimum unit in an analysis of lightness distribution described above.

The size of a minimum unit in an analysis of lightness distribution is selected so that the surface contamination is represented most effectively and efficiently. It is preferable to select the size of a minimum unit in an analysis of lightness distribution to be 1$\frac{1}{10}$ times the size of contamination to be evaluated so that the surface contamination may be represented most effectively and efficiently. It is not preferable that the ratio of the size of a minimum unit to that of contamination is larger than 1, because the resolution in the representation of contamination, i.e., an evaluation accuracy becomes low. It is also not preferable that the ratio of the size of a minimum unit to that of contamination is lower than $\frac{1}{10}$, because an evaluation accuracy does not become so high compared with the increasing of the amount of information to be processed. The dot size of 0.25 mm×0.25 mm is selected in the example described above. This is because the size of deposition contamination to be evaluated is 0.5 mm×0.5 mm, so that the surface contamination may be most effectively and efficiently represented when the minimum unit in the lightness distribution analysis is selected to be $\frac{1}{2}$ times the size 0.5 mm×0.5 mm.

The central processing unit obtains lightness every dot of the dot matrix (Step S2), thereby a lightness data for 400×400 dots is obtained. The lightness data is stored in the memory.

Figure 15:
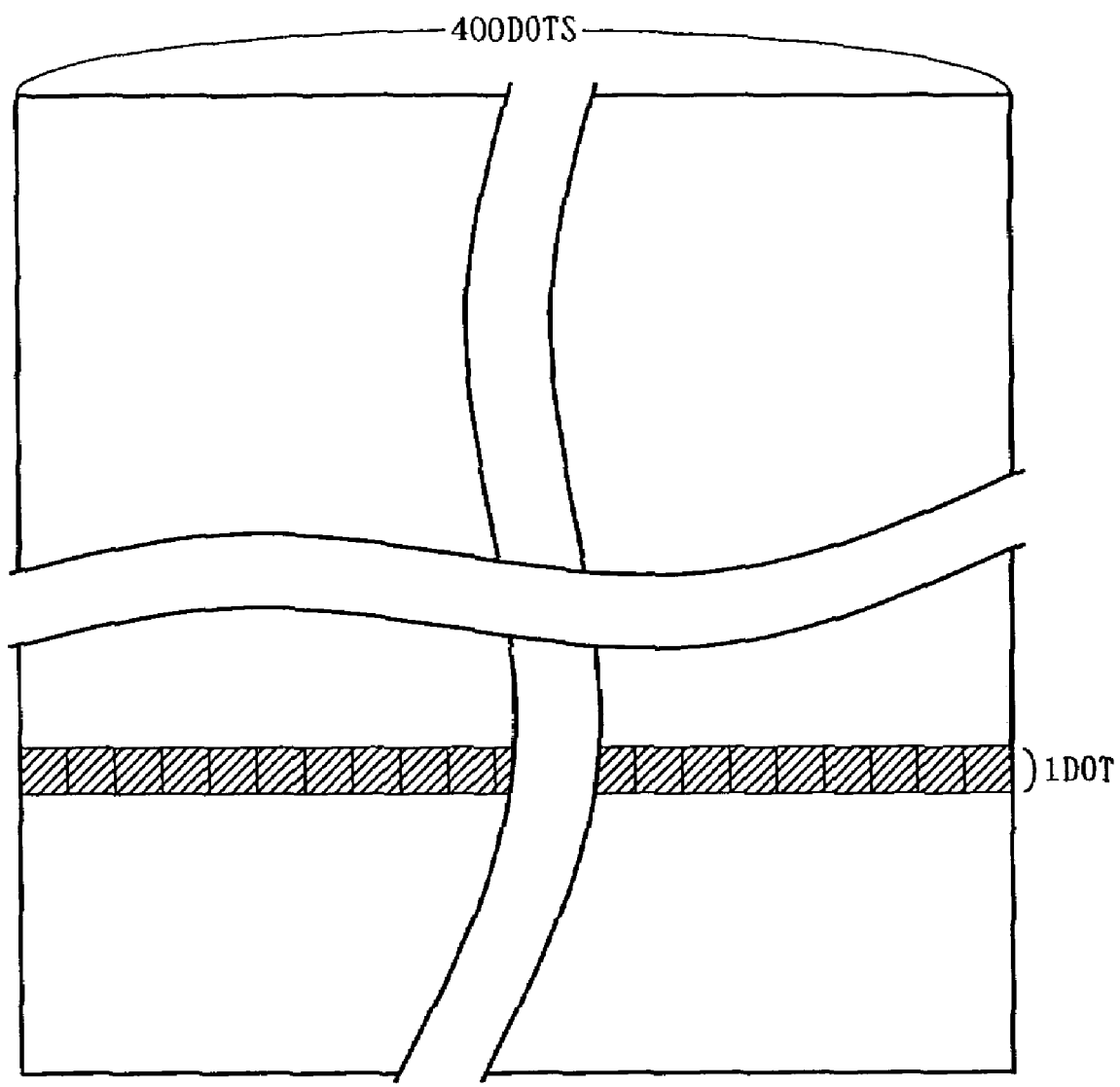
FIG. 15 shows the area to be measured in the dot matrix.

Next, "contamination index" denoting the level of surface contamination of a window glass plate is analyzed from the lightness data. At first, an inspector displays a monochromatic image on the display and selects the contaminated area to be analyzed while looking at the monochromatic image on the display (Step S3). The contaminated area to be analyzed is one-dimensional region extending in an X-direction on the display, i.e., one-dimensional region having 400-dot width in an X-direction and 1-dot width in a Y-direction on the dot matrix in FIG. 14. In FIG. 15, the area to be evaluated in the dot matrix is shown by a hatched region.

The central processing unit of the computer acquires the lightness data of selected one-dimensional region from the memory (Step S4), and scans said one-dimensional region to create a lightness distribution data (Step S5). The central processing unit may form a graph of lightness distribution from the one-dimensional lightness distribution data to display it on the display. The lightness distribution has dispersion based on the surface contamination of a window glass plate, which dispersion may be recognized in a visual manner from the lightness distribution graph.

The central processing unit calculates a standard deviation which is an index showing the level of dispersion of lightness (Step S6). In the present invention, the standard deviation is used as "a contamination index" for evaluating the contamination. Lager the standard deviation of lightness, higher the level of contamination becomes. Therefore, an inspector may recognize the level of contamination for a window glass plate from "a contamination index".

Embodiments of a method for evaluating the contamination according to the present invention will now be described.

EMBODIMENT 1

A self-cleaning glass plate (i.e., a thin film including titanium oxide is formed thereon) and an ordinary float glass plate are contaminated by an accelerated contamination test and are analyzed for comparison by means of a contamination evaluating method described hereinbefore.

Contaminated glass plate samples used for the analysis are made as follows. Glass plate samples of a self-cleaning glass plate and an ordinary float glass plate are prepared. The glass plate samples are cleaned by an ultrasonic cleaning in ethanol (40° C., 10 minutes), are cleaned using a sponge including a detergent for glass (Goods Name; Glass Mypet, made by Kao Company Ltd.), and completely linsed by water. The water on the samples is wiped by a non-woven fabric cloth (Goods Name; Bencot, made by Asahikasei Company Ltd.), and the samples are illuminated by ultraviolet (UV) light (a black light lamp is used, 3 mW/cm$^2$, 2 hours).

Contaminated liquid is sprayed on the samples for three seconds by means of an electric spray gun from the position where 800 mm is far from the samples. The contaminated liquid consists of pure water in which contaminants (carbon black 5%, yellow ocher 67.5%, baked loam 22.5%, and silica powder 5.0%) are dispersed in solid concentration of 0.03%, the contaminants being defined in Japanese Industrial Standards (JISZ8901). Subsequently, the surfaces of the samples are dried by means of a dryer for two minutes. The spray and dry steps described above are repeated ten times. The color images of the self-cleaning glass plate samples and ordinary float glass plate samples thus contaminated are taken by means of the camera and are displayed on the computer display. According to the visual impression of an inspector for the image on the display, the contamination for the float glass plate samples has nonuniformity and the level of contamination for the float glass plate sample is larger than that of the self-cleaning glass plate sample.

Figure 17A:
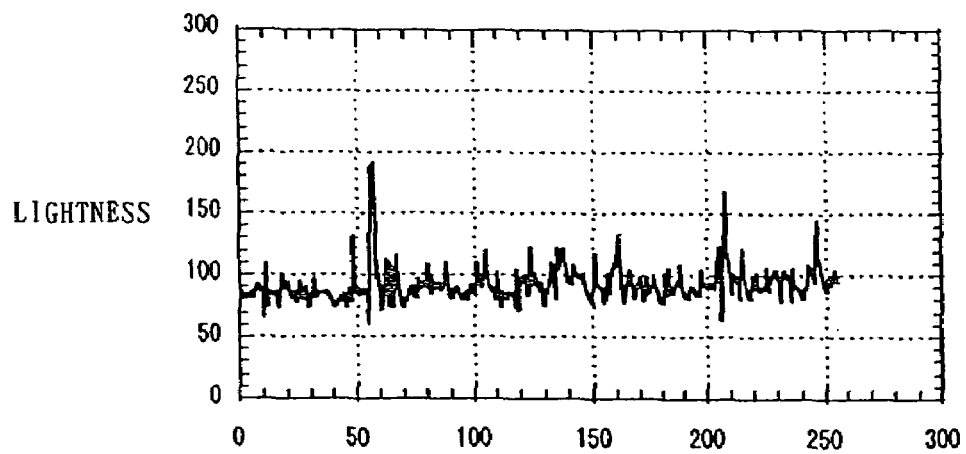
FIGS. 17A and 17B show the graphs illustrating the lightness distribution.
Figure 17B:
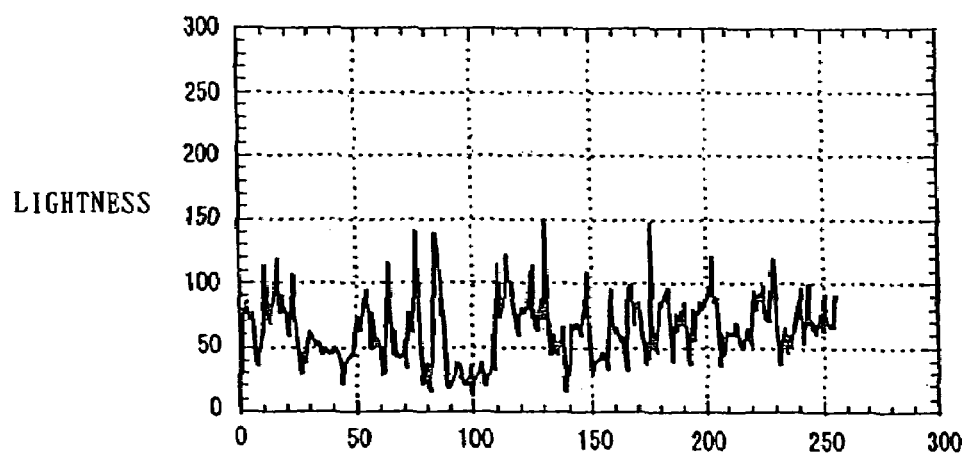

Referring to FIGS. 16A and 16B, there are shown the monochromatic images of the self-cleaning glass plate sample and ordinary float glass plate sample processed by the personal computer and displayed on a display, respectively. Referring to FIGS. 17A and 17B, there are shown the graphs illustrating the lightness distribution in one-dimensional region (255 dots) which is an analyzing area in an X-direction selected in the monochromatic image. It is understood from the lightness distribution graphs that the dispersion of the lightness of the ordinary float glass plate sample is larger than that of the self-cleaning glass plate sample. "Contamination indexes" calculated by the computer are 24.9 for the self-cleaning glass plate sample and 34.9 for the ordinary float glass plate sample, respectively. Calculated contamination indexes are matched to the visual impressions of an inspector for the monochromatic images on the display.

EMBODIMENT 2

Figure 18:
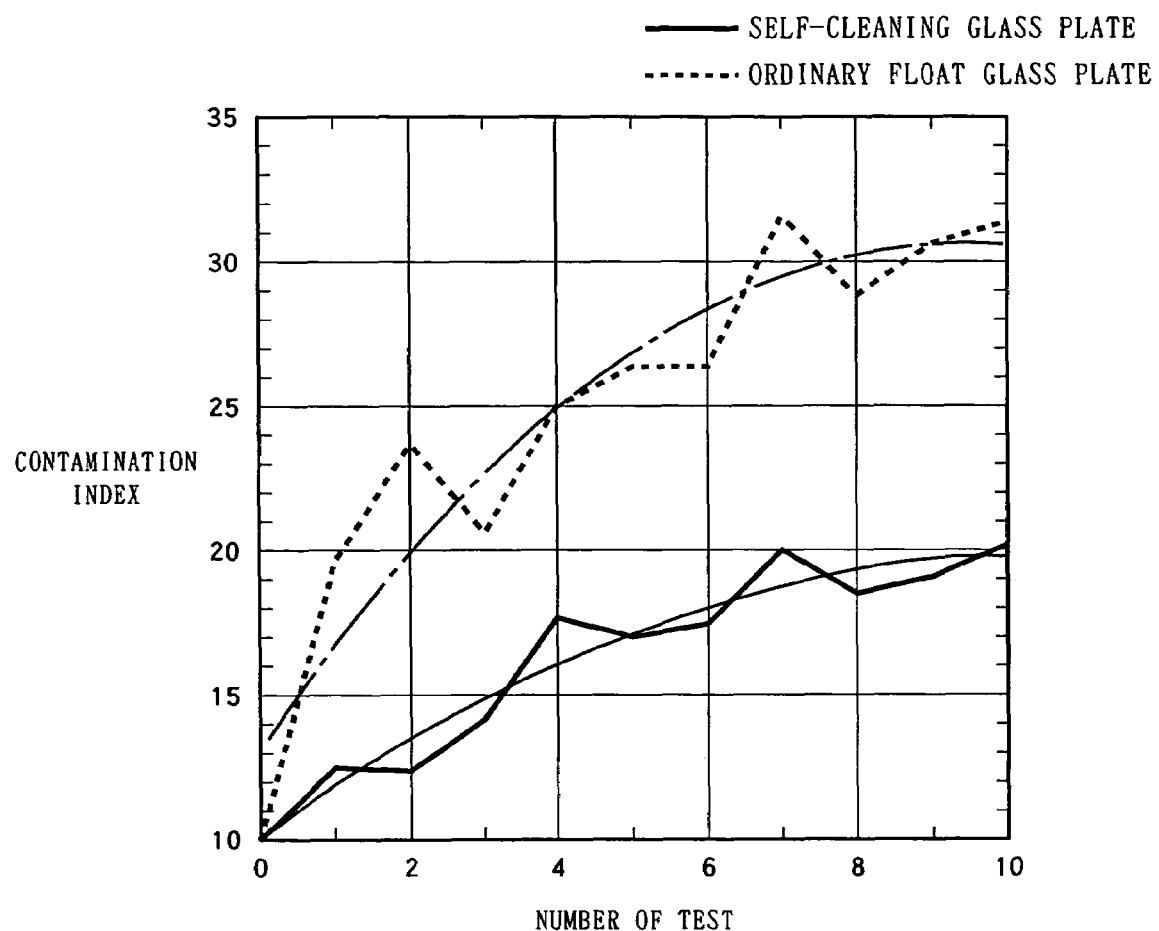
FIG. 18 shows the graph in which the results of the analysis are plotted.

The contaminations of a self-cleaning glass plate sample and ordinary float glass plate sample are changed based on the number of accelerated contamination tests, and are analyzed by means of a contamination evaluation method described hereinbefore. FIG. 18 shows the graph in which the results of the analysis are plotted.

According to this graph, it is understood that the level of contamination is proceeded as the number of accelerated contamination tests is increased, and the speed of the contamination of the ordinary float glass plate sample is faster than that of the self-cleaning glass plate sample.

EMBODIMENT 3

Figure 20A:
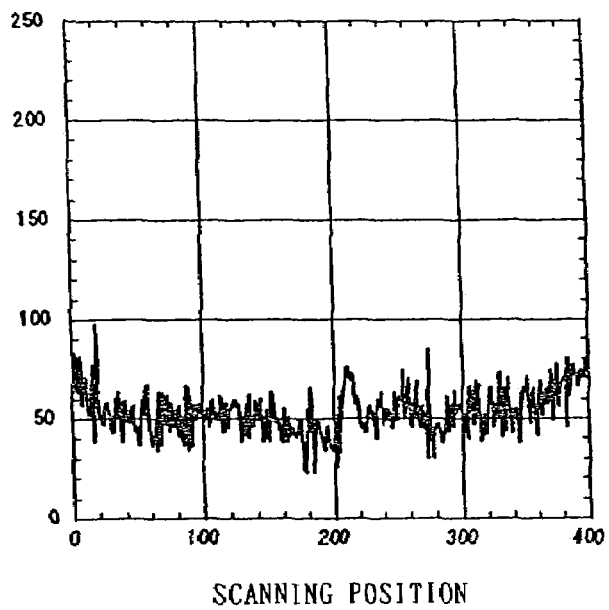
FIGS. 20A and 20B show the graphs illustrating the lightness distribution.
Figure 20B:
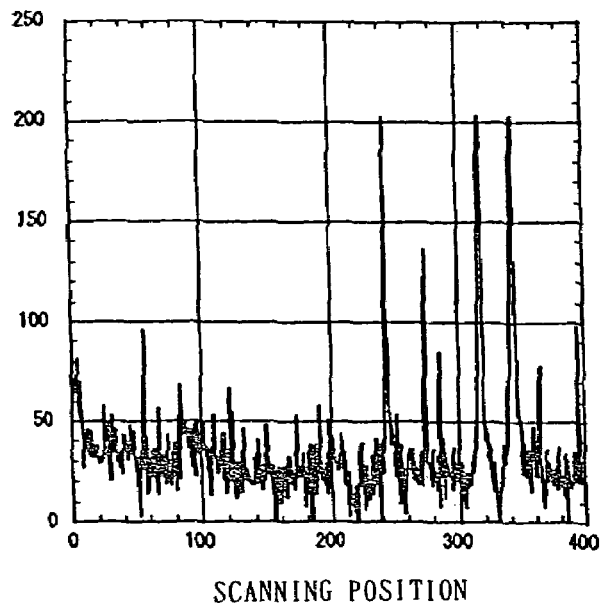

The contamination evaluating method described in the embodiments is applied to a glass plate which has the scratch contamination. Referring to FIGS. 19A and 19B, there are shown the monochromatic images of two ordinary glass plate samples having no scratches and having scratches, respectively, the monochromatic images being formed by the personal computer and displayed on the display. Referring to FIGS. 20A and 20B, there are shown the graphs indicating the lightness distribution in one-dimensional region which is an analyzing area in an X-direction selected in the monochromatic image. It is understood from the lightness distribution graphs that the lightness in the area having scratches is largely varied. "Contamination indexes" calculated by the computer are 11.23 for the glass plate sample having no scratches and 30.68 for the glass plate sample having scratches. It is understood that a contamination index becomes large when the glass plate sample has scratches thereon.

While the minimum unit in an analysis of lightness distribution is 0.25 mm×0.25 mm in this embodiment, the size of the minimum unit may be changed based on the size (width) of scratch. The size of the minimum unit may be 1$\frac{1}{10}$ times the size of scratch to be evaluated.

COMPARISON EXAMPLE

Comparison examples will now be described in which the conventional evaluation method and the evaluation method according to the present invention are applied to four kinds of glass plate samples.

Four kinds of samples A, B, C and D shown in FIG. 21 are prepared as the objects to be evaluated. The samples A, B and C are ordinary float glass plates, and the sample D is a self-cleaning glass plate.

For the sample A, the cleaning step of a glass plate and the spraying step of contaminated liquid to a glass plate are not conducted. For the samples B, C and D, step of cleaning of a glass pate is not conducted, and the step of spraying of contaminated liquid to a glass plate and drying thereof is repeated one time, ten times, and one time, respectively.

According to visual impression to these samples, the samples A, B and C look like contaminated in this order. While the level of contamination for the sample D is substantially the same as the sample B, the sample B looks like more contaminated than the sample D in a visual impression.

Transmittance, haze factor, and color difference are measured in a conventional evaluation method. These measured values are shown in Table 1 together with the values of contamination indexes obtained by the evaluation method according to the present invention. The values of contamination indexes are obtained by measuring contamination indexes of ten lines of one-dimensional region (399 dots) at intervals of 1 cm and averaging them in order to evaluate two dimensional distribution.

TABLE 1

| | Sample | | | | |
|---|---|---|---|---|---|
| | A | B | C | D | |
| Transmittance (%) | 91.3 | 91.2 | 90.4 | 78.4 | SUGA Haze Meter (Average of 5 measured values) |
| Haze factor (%) | 0.1 | 0.9 | 5.4 | 2.4 | SUGA Haze Meter (Average of 5 measured values) |
| Color difference | 27.4 | 27.7 | 29.0 | 48.7 | MINOLTA CR300 (Average of 5 measured values) |
| Contamination Index | 18.1 | 30.6 | 39.6 | 21.4 | |

The transmittance and haze factor are obtained by measuring five points using SUGA Haze Metar and averaging measured values. The color difference is obtained by measuring five points using MINOLTA CR3000 and averaging measured values.

There is no difference in transmittance between the samples A and B, while there is a large difference in transmittance between the samples B and D the levels of contamination thereof are substantially the same. Therefore, it is understood that the transmittance is largely controlled by the transmittance of a glass plate itself and is not suitable for the contamination evaluation.

The haze factor is correlated to the level of contamination where the kinds of glass plates are the same, but is not correlated to the level of contamination where the kinds of glass plates are different. The color difference is largely controlled by the perceived color of a glass plate itself and is not suitable for the contamination evaluation.

Contamination indexes according to the present invention are 18.1 for the sample A, 30.6 for the sample B, 39.6 for the sample C, and 21.4 for the sample D, respectively. These contamination indexes are matched to the visual impressions for contamination.

EMBODIMENT 4

In the embodiments described above, the standard deviation of lightness of an object to be evaluated are used as contamination indexes for evaluating the contamination. However, when severely contaminated objects are compared to each other, there is a case such that the relation between a visual evaluation and a contamination index is reversed. Accordingly, when objects each having contamination index larger than a predetermined value are compared to each other, the standard deviation of maximal lightness value of an object to be evaluated is used as a second contamination index.

The standard deviation of maximal lightness value means, herein, a standard deviation of a series of data consisting of maximal values derived from the lightness data. That is, where there are many contaminated areas which are bright, the glass plate looks like more contaminated as the areas each having a maximal lightness have a large irregularity in their lightness.

An example of evaluation using a second contamination index will now be described. Three kinds of contaminated samples E, F and G are prepared as objects to be evaluated. The samples E, F and G are ordinary float glass plates. These contaminated samples are prepared by contaminating the surfaces of the glass plates in a manner described in the embodiment 1. According to the visual impression to these samples, the samples E, F and G look like contaminated in this order.

Figure 23A:
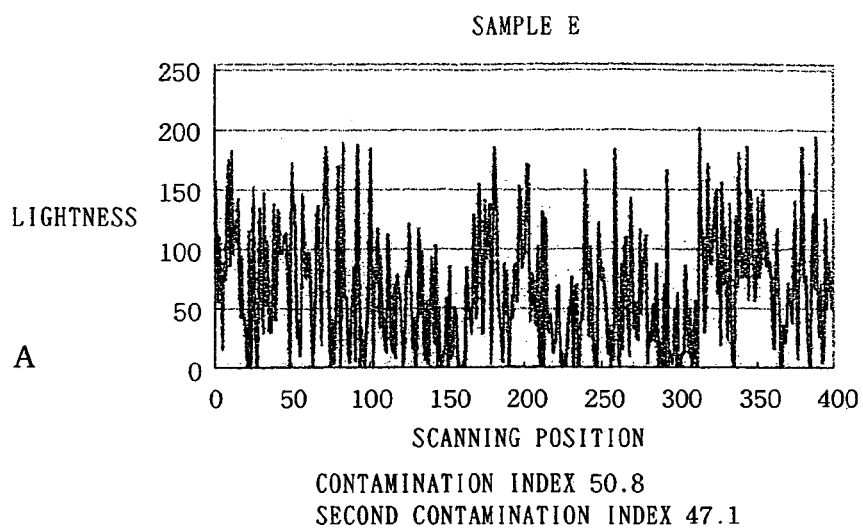
FIGS. 23A, 23B and 23C show the graphs illustrating the lightness distribution.
Figure 23B:
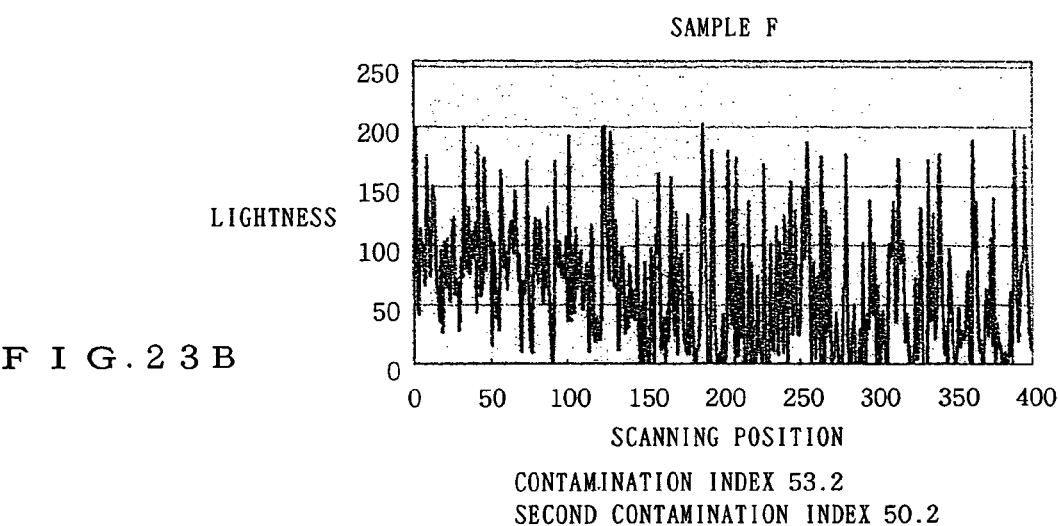
Figure 23C:
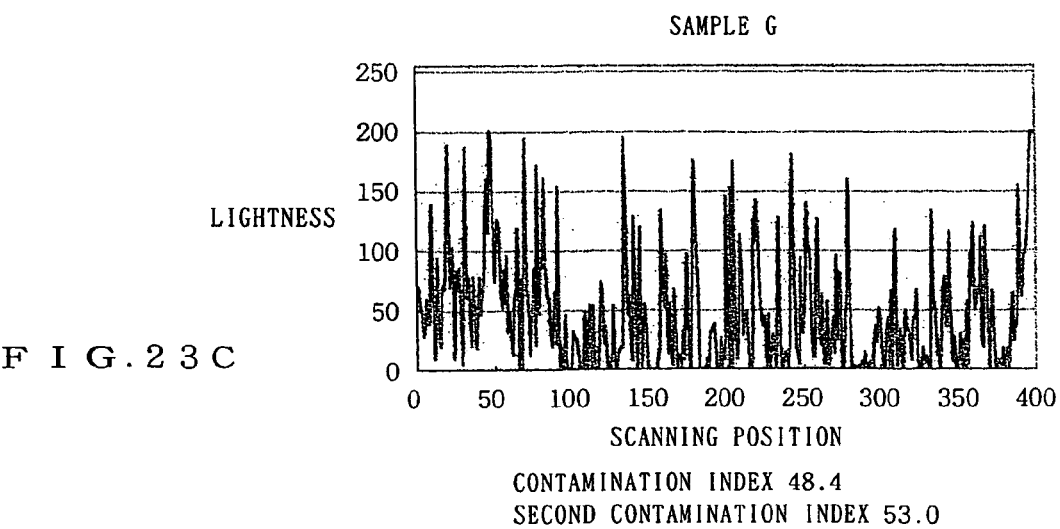

Referring to FIG. 22, there are shown the monochromatic images of the contaminated samples E, F and G processed by the personal computer and displayed on a display, respectively. Referring to FIGS. 23A, 23B and 23C, there are shown the graphs indicating the lightness distribution in one-dimensional region (255 dots) which is an analyzing area in an X-direction selected in the monochromatic image. Contamination indexes calculated by the computer are 50.8 for the sample E, 53.2 for the sample F, and 48.4 for the sample G, respectively. A visual evaluation and a contamination index show an opposite relation in the samples F and G.

The second contamination indexes are calculated by the computer, resulting in 47.1 for the sample E, 50.2 for the sample F, and 53.0 for the sample G, respectively. A visual evaluation and a second contamination index show a matched relation in the samples F and G.

As a result, it is appreciated that the second contamination index is used for the criterion for an evaluation of the contamination when objects to be evaluated each thereof has a contamination index larger than 40 are compared.

INDUSTRIAL APPLICABILITY

According to a contamination evaluation method of the present invention, an inspector may optionally select an area to be evaluated. If an area to be selected is not changed, analysis data has a repeatability. It is therefore possible to realize the quantification of contamination which is close to the visual impression of human being. According to the method of the present invention, an analysis is conducted by varying a minimum unit in analysis of lightness distribution based on the size of contamination to be valuated such as deposits and scratches, so that the difference in a surface contamination is clearly represented.

An imaging box of the present invention may be easily set because the box is integrated with a camera. The positional relation among a camera, an object, and a light source is fixed by using the imaging box, so that the condition of taking an image is highly repeatable. Furthermore, the portability and mobility of the imaging box is high, so that it is possible to take an image of a surface of a window glass or wall of a building.

The invention claimed is:

1. A method for evaluating the contamination of a surface of an object comprising the steps of:
    taking a color image of the surface of the object;
    converting a color image data denoting the color image obtained by the step of taking an color image into a monochromatic image data;
    dividing a monochromatic image denoted by the monochromatic image data into a dot matrix to obtain lightness per dot;
    selecting an area to be evaluated on the dot matrix;
    calculating a standard deviation of lightness from the distribution of lightness of the selected area as a contamination index; and
    evaluating the contamination based on the contamination index.

2. A method for evaluating the contamination of a surface of an object comprising the steps of:
    taking an image of the surface of the object;
    dividing the image obtained by the step of taking an image into a dot matrix to obtain lightness per dot;

selecting an area to be evaluated on the dot matrix;

calculating a standard deviation of lightness from the distribution of lightness of the selected area as a first contamination index;

calculating a standard deviation of lightness from the distribution of lightness of the selected area as a first contamination index;

calculating a standard deviation of maximal value of lightness from the distribution of maximal value of lightness of the selected area as a second contamination index, when the first contamination index is a larger than a predetermined value; and evaluating the contamination based on the second contamination index.

3. A method for evaluating the contamination of a surface of an object comprising the steps of:

taking a color image of the surface of the object;

converting a color image data denoting the color image obtained by the step of taking an color image into a monochromatic image data;

dividing a monochromatic image denoted by the monochromatic image data into a dot matrix to obtain lightness per dot;

selecting an area to be evaluated on the dot matrix;

calculating a standard deviation of lightness from the distribution of lightness of the selected area as a first contamination index;

calculating a standard deviation f maximal value of lightness from the distribution of maximal value of lightness of the selected areas as a second contamination index, when the first contamination index is larger than a predetermined value; and evaluating the contamination based on the second contamination index.

4. A method according to any one of claims 1-3 wherein the area to be evaluated is a one-dimensional region.

5. A method according to claim 4 wherein the size of the dot is selected to be 1 1/10 times the size of contamination to be evaluated.

6. A method according to any one of claims 1-3 wherein the area to be evaluated is a two-dimensional region.

7. A method according to claim 6 wherein the size of the dot is selected to be 1 1/10 times the size of contamination to be evaluated.

8. A method according to any of claims 1-3 wherein the step of taking an image of the surface of the object is conducted by a solid state imaging camera.

9. A method according to any of claims 1-3 wherein the step of taking an image of the surface of the object is conducted by an optical camera.

10. A method according to claim 1 wherein the steps of converting a color image data denoting the obtained color image into a monochromatic image data denoting the obtained color image into a monochromatic image data, dividing a monochromatic image denoted by the monochromatic image data into a dot matrix to obtain lightness per dot, selecting an area to be evaluated on the dot matrix, and calculating the contamination index from the distribution of lightness of the selected area are conducted in an image processing apparatus.

11. A method according to claim 2 wherein the steps of dividing the obtained image into a dot matrix to obtain lightness per dot, selecting an area to be evaluated on the dot matrix, and calculating the first contamination index from the distribution of lightness of the selected area and the second contamination index of maximal value of lightness from the distribution of maximal value of lightness of the selected area are conducted in an image processing apparatus.

12. A method according to claim 3 wherein the steps of converting a color image data denoting the obtained color image into a monochromatic image data, dividing a monochromatic image denoted by the monochromatic image data into a dot matrix to obtain lightness per dot, selecting an area to be evaluated on the dot matrix, and calculating the first contamination index from the distribution of lightness of the selected area and the second contamination index of maximal value of lightness from the distribution of maximal value of lightness of the selected area are conducted in an image processing apparatus.

13. A method according to any one of claims 10-12 wherein the image processing apparatus is a personal computer.

* * * * *